United States Patent
Vilkomerson et al.

(10) Patent No.: US 9,166,141 B2
(45) Date of Patent: Oct. 20, 2015

(54) PROCESS OF MANUFACTURING A PIEZOPOLYMER TRANSDUCER WITH MATCHING LAYER

(71) Applicant: DVX, LLC, Princeton, NJ (US)

(72) Inventors: David Vilkomerson, Princeton, NJ (US); Thomas Chilipka, East Windsor, NJ (US)

(73) Assignee: DVX, LLC, Princeton, NJ (US)

( * ) Notice: Subject to any disclaimer, the term of this patent is extended or adjusted under 35 U.S.C. 154(b) by 46 days.

(21) Appl. No.: 14/028,578

(22) Filed: Sep. 17, 2013

(65) Prior Publication Data

US 2015/0044386 A1  Feb. 12, 2015

Related U.S. Application Data

(63) Continuation-in-part of application No. 13/593,565, filed on Aug. 24, 2012, now Pat. No. 8,564,177.

(51) Int. Cl.
*H01L 41/22* (2013.01)
*H01L 41/29* (2013.01)
(Continued)

(52) U.S. Cl.
CPC ............... *H01L 41/22* (2013.01); *B06B 1/067* (2013.01); *B06B 1/0688* (2013.01);
(Continued)

(58) Field of Classification Search
CPC ..... H01L 41/183; H01L 41/193; H01L 41/22; H01L 41/29; H01L 41/314; H01L 41/37; H01L 41/45; H01L 41/257; H01L 41/317; B06B 1/067; B06B 1/0688; A61B 8/4483; A61B 8/4494; A61B 8/4272; A61B 8/4281; H05K 9/0094; H03H 3/04; Y10T 29/42

USPC .......... 29/25.35, 594, 846; 427/58, 100, 260; 252/62.9 PZ; 310/334, 335, 365; 367/180, 181; 174/389

See application file for complete search history.

(56) References Cited

U.S. PATENT DOCUMENTS 4,701,659 A * 10/1987 Fujii et al. ............. B06B 1/0688
4,756,808 A    7/1988 Utsumi et al.
(Continued)

FOREIGN PATENT DOCUMENTS

JP         01068981 A  *  3/1989  ............... 29/25.35 X

OTHER PUBLICATIONS

G. Kino, Acoustic Waves: Devices, Imaging and Analog Signal Processing, Prentice-Hall, 1987, p. 12.
(Continued)

*Primary Examiner* — A. Dexter Tugbang
(74) *Attorney, Agent, or Firm* — Scientific Works, LLC; Yue Ma

(57) ABSTRACT

Matching layers improve the performance of ultrasonic transducers. Such layers have traditionally required significant effort and expense to be added to ultrasonic transducers. The present invention discloses a method of producing ultrasonic transducers with a matching layer, specifically for ultrasonic transducers utilizing piezopolymer transducer materials. Rather than the conventional method of forming the piezopolymer on a substrate and then attaching a matching layer through which the transducer emits its ultrasound energy, we teach depositing the piezopolymer on a substrate that also serves as a matching layer through which the ultrasound is emitted. We also teach depositing an additional shield layer for reducing electromagnetic interference. Methods of how to select materials and modify their ultrasonic characteristics are also discussed.

15 Claims, 4 Drawing Sheets

(51) Int. Cl.
*H01L 41/317* (2013.01)
*H01L 41/45* (2013.01)
*H01L 41/18* (2006.01)
*H01L 41/314* (2013.01)
*H01L 41/37* (2013.01)
*B06B 1/06* (2006.01)
*H01L 41/193* (2006.01)
*H01L 41/257* (2013.01)
*A61B 8/00* (2006.01)
*H05K 9/00* (2006.01)
*H03H 3/04* (2006.01)

(52) U.S. Cl.
CPC ........... *H01L 41/183* (2013.01); *H01L 41/193* (2013.01); *H01L 41/257* (2013.01); *H01L 41/29* (2013.01); *H01L 41/314* (2013.01); *H01L 41/317* (2013.01); *H01L 41/37* (2013.01); *H01L 41/45* (2013.01); *A61B 8/4272* (2013.01); *A61B 8/4281* (2013.01); *A61B 8/4483* (2013.01); *A61B 8/4494* (2013.01); *H03H 3/04* (2013.01); *H05K 9/0094* (2013.01); *Y10T 29/42* (2015.01)

(56) References Cited

U.S. PATENT DOCUMENTS

| | | | |
|---|---|---|---|
| 5,254,504 A * | 10/1993 | Van der Spiegel et al. | 427/100 X |
| 6,278,224 B1 * | 8/2001 | Sawada et al. | 310/334 |
| 8,156,620 B2 | 4/2012 | Habu et al. | |
| 2001/0015279 A1 * | 8/2001 | Marutsuka | 174/389 X |
| 2002/0027400 A1 | 3/2002 | Toda | |
| 2002/0050768 A1 | 5/2002 | Beck et al. | |
| 2002/0109565 A1 * | 8/2002 | Ella et al. | H03H 3/04 |
| 2004/0085858 A1 * | 5/2004 | Khuri-Yakub et al. | 367/181 |
| 2006/0154075 A1 * | 7/2006 | Kuniyasu et al. | 427/58 X |
| 2008/0177139 A1 * | 7/2008 | Courtney et al. | A61B 8/4281 |
| 2010/0026141 A1 * | 2/2010 | Osawa | 310/335 |
| 2010/0066207 A1 | 3/2010 | Saito | |
| 2011/0050039 A1 | 3/2011 | Toda et al. | |

OTHER PUBLICATIONS

Ohigashi, et al, Piezoelectric and Ferroeectric properties of P[VDF-TrFE] Copolymers and Their Application to Ultrasonic Transducers, in Medical Applications of Piezoelectric Polymers, Ed. by P.Galletti et al, Gordon and Breach Science Publishers, New York, 1988.

M. Toda and M. Thompson, "Novel Multi-Layer Polymer-Metal Structures for Use in Ultrasonic Transducer Impedance Matching and Backing Absorber Applications", IEEE Transaction on Ultrasonics, Ferroelectrics and Frequency Control, vol. 57, No. 12, pp. 2818-2827, 2010.

Handbook of Chemistry and Physics, 42nd Edition, C.D. Hodgman, Ed., Chemical Rubber Company, Cleveland, 1960, p. 2588.

* cited by examiner

PROCESS OF MANUFACTURING A PIEZOPOLYMER TRANSDUCER WITH MATCHING LAYER

CROSS-REFERENCE TO RELATED APPLICATIONS

This application is a continuation-in-part of U.S. application Ser. No. 13/593,565, filed Aug. 24, 2012, which also claims the benefit of U.S. Provisional Application Ser. No. 61/532,643, filed on Sep. 9, 2011, both hereby incorporated by reference.

REFERENCE TO GOVERNMENT FUNDING

This application was made with partial Government support under contract 2R44HL071359 awarded by the NHLBI of the National Institute of Health. The Government has certain rights in this invention.

FIELD OF THE INVENTION

This invention relates to the structure and fabrication of ultrasonic transducers, particularly the structure and fabrication method for piezopolymer transducers and the application of matching layer.

BACKGROUND OF THE INVENTION

Ultrasound is widely used in medical diagnosis for imaging of tissues, e.g. human fetus in utero, and measuring the velocity of blood and heart motion by means of Doppler shift of the backscattered ultrasound. In such applications, it is desirable that the ultrasound transducer is as sensitive as possible, thus maximizing the signal energy used to produce the image or measure the tissue velocity. As the available transducer materials that generate and receive ultrasound signals are of different acoustic impedances than human tissue, "matching" between the tissue and the transducer is necessary to maximize the signal that is received. For this reason, use of a "matching layer" is known to those skilled in the art of making ultrasound transducers. Using a transducer matching layer is the application to ultrasound devices of the same theory as employed in optics for anti-reflection coatings or for matching networks in electronics: increasing the amount of energy that enters a desired medium from driving source by reducing the energy reflected back caused by a mismatch in impedances between the driving impedance and the propagating medium's impedance.

It can be shown (for example, in G. Kino, Acoustic Waves: Devices, Imaging and Analog Signal Processing, Prentice-Hall, 1987, page 12) that to maximize the amount of acoustic energy of wavelength $\lambda$ from a transducer of impedance Zt into a medium of impedance Zm, a layer is required with the characteristics of being one-quarter wavelength thick and having an acoustic impedance of $(Zt \cdot Zm)^{1/2}$, i.e. of impedance equal to the square root of the product of the transducer impedance and the medium impedance. This is the same relation as needed to match electromagnetic transmission lines.

A matching layer is widely used in ultrasonic transducers for medical imaging, for example, as taught by Utsumi et al in U.S. Pat. No. 4,756,808. This is because of the large impedance difference between the most commonly used piezoelectric material for medical ultrasonic transducers such as the ceramic PZT (Lead Zirconate Titanate), and human tissue. The unit of acoustic impedance is Rayl—named after Lord Rayleigh—in units of kg/m$^2$-sec. PZT has an impedance of 20-40×10$^6$ rayl (i.e. 20-40 MRayl), while the acoustic impedance of tissue is 1.5 MRayl, leading to poor transfer of energy into tissue, as needed for medical imaging, unless a matching layer is used. Therefore, most medical imaging transducers have a matching layer attached to their outer surface to increase the transducer's sensitivity by improving coupling between PZT and human tissue.

Piezoelectric materials include a number of piezoplastic materials, e.g. PVDF, Nylon 8, vinylcyanide-vinylacetate copolymer, of which the most acoustically efficient is P(VDF$_x$-TrFE$_{100-x}$), a copolymer. When x, the percentage of VDF in the copolymer, is in the range of 65-82 mol % which is the desirable range for transducer operation (See Ohigashi, et al, Piezoelectric and Ferroeectric properties of P[VDF-TrFE] Copolymers and Their Application to Ultrasonic Transducers, in *Medical Applications of Piezoelectric Polymers*, Ed. by P. Galletti et al, Gordon and Breach Science Publishers, New York, 1988), the copolymer can be dissolved and spin-coated or dipped onto a substrate, and after annealing and polarizing, will form a light, flexible, piezoelectric film. While not as efficient a transducer material as ceramic PZT ($k_T^2$, the measure of conversion of electrical to acoustic energy for copolymer is about ⅓rd that of PZT), the copolymer has the advantages of ease of fabrication, lightness, and flexibility that make it desirable in certain situations. Moreover, because of the copolymer's low planar coupling, individual transducers elements can be defined by placement of metal electrodes, in contrast to PZT, whose high planar coupling requires mechanical grooves to be cut between elements to allow them to function independently. Particularly, the ease of making transducer elements by, for example, simple photolithographic deposition of metal electrodes rather than by mechanical grooving of micron-size cuts is an important advantage at higher frequencies, e.g. from 5 MHz to 30 MHz, where the dimension of the individual transducer elements needed to direct an ultrasound beam must be a fraction of the 50-500 micron acoustic wavelength. Furthermore, it is hard to fabricate these very thin, e.g. 250-25 micron thick for the 5-50 MHz range, ceramic transducers.

Another advantage of the P(VDF-TrFE) copolymer material is that its acoustic impedance is about 4.5 MRayl, much closer to the impedance of water (or tissue) of 1.5 MRayl than PZT's ~35 MRayl. Note that while the mismatch is much smaller, there is still a substantial 3:1—mismatch between the impedances, so a matching layer would still improve the coupling between such a copolymer piezoplastic transducer and tissue.

However, while this copolymer has been used as a transducer for two decades, matching layers have been rarely used. At the high frequencies for which piezoplastic transducers are particularly advantageous, attaching such layers to a piezoplastic layers with minimal bond thickness—so as not to affect the matching—is extremely difficult. Therefore, although there has been development of piezoplastic transducers, such as taught in U.S. Pat. No. 6,641,540 to Fleisschman et al, or U.S. Pat. No. 8,156,620 to Habu et al, matching layers are not included in their fabrication.

With reference to FIG. 1A, in the conventional structure of a piezoplastic ultrasonic transducer 100, a layer of piezopolymer 130, is spin-coated (or dipped, or electro sprayed etc, as is known in the art) onto a substrate, 110, on which there is an electrode layer 120. A second electrode layer, 121, is formed on top of the piezopolymer to complete the transducer.

Recently M. Toda taught in published US patent applications 2002/0027400 and 2011/0050039 ways of combining polymer films and metal films to provide composite matching layers for piezoceramic or piezoplastic resonant transducers. This provides means of synthesizing composite layers of desired acoustic characteristics. Toda teaches using a polymer layer attached to the piezo-element upon which is placed a metal layer between the polymer-element of the synthesized matching layer and the medium into which the acoustic energy is to propagate. With reference to FIG. 1B, a matching layer 140 was added by means of an adhesive layer 135, for example as discussed by Toda. However, the addition of a thin bonding layer reduces the flexibility of the structure and increases the difficulty of fabrication and cost of the transducer. An improved structure and fabrication method of transducer is further needed.

SUMMARY OF THE INVENTION

According to the present invention an easy fabrication method for making a piezopolymer ultrasound transducer is provided, in which the order of fabricating in the conventional method is reversed: we form an electrode pattern onto a matching layer (where the metallic mass of the electrode pattern is controlled to "tune" the matching layer, as will be described later), and then by spin-coating dipping, electro-spraying, or other usual ways, fabricating a layer of piezopolymer directly onto the matching layer, i.e. the substrate is both substrate and the matching layer. We then place a sheet electrode directly on the piezopolymer for poling, and after poling, as a ground electrode. In such way, we have gained the advantages of a copolymer transducer with matching layer, while making the fabrication much easier by using a substrate that is also a matching layer. Further layers can be placed on top of the ground electrode (i.e. opposite the matching layer/substrate) to further increase the efficiency of the transducer by acting as a backing, as is known by those skilled in the art.

According to another aspect of the present invention, a flexible structure of a ultrasound transducer is provided such that it can be used to make cylindrical transducers for measuring velocity of fluid such as taught in U.S. patent application Ser. No. 13/358,507, filed on Jan. 25, 2012.

According to another aspect of the present invention, the present invention is useful in medical imaging applications using ultrasonic transducer. Examples of these applications include measuring the velocity of blood stream in a vessel or measuring the velocity of any fluid carrying ultrasound scattering particles, and for fabrication of low cost and/or flexible ultrasonic transducers for imaging as well as Doppler use.

According to another aspect of the present invention, a "shielding" is placed on the substrate/matching layer to reduce the noise caused by electromagnetic interference (EMI). Other applications may also become apparent as utilized by one skilled in the art.

BRIEF DESCRIPTION OF THE DRAWINGS

The present invention will become more fully understood from the detailed description and the accompanying drawings, wherein.

DETAILED DESCRIPTION

Figure 1A:
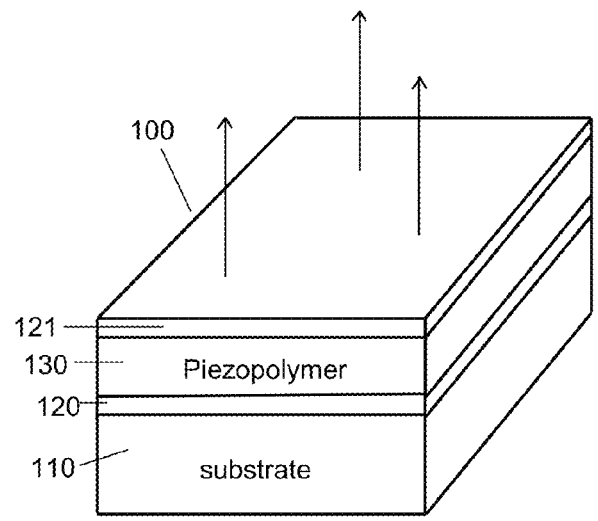
FIG. 1A shows a conventional structure of a piezoplastic ultrasonic transducer without a matching layer. The arrows indicate the direction of the ultrasound propagation into the medium.
Figure 1B:
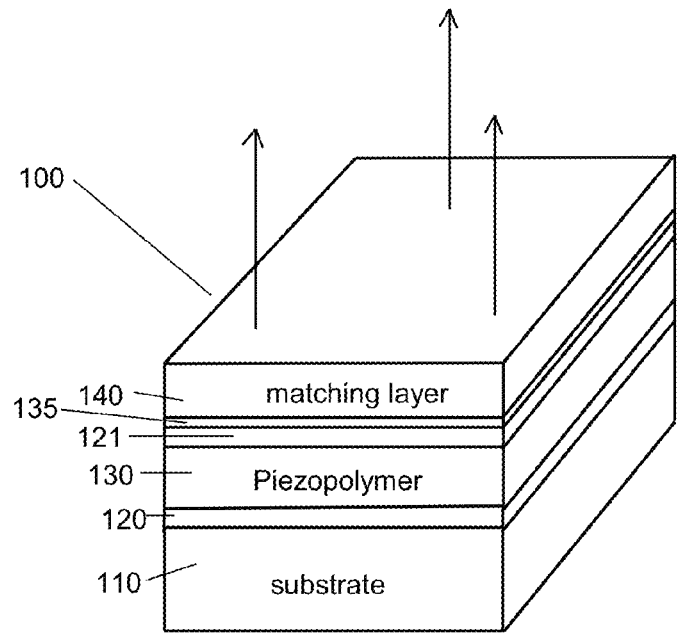
FIG. 1B shows a conventional structure of a piezoplastic ultrasonic transducer with a matching layer. The arrows indicate the direction of the ultrasound propagation into the medium.

We disclose here the method of designing a transducer by means of a design and construction example according to the present invention. This example, however, is not intended to limit the scope of the present invention.

For purposes of example, we will consider a transducer intended to operate in the range of frequencies around 25 MHz, using P(VDF$_{75}$–TrFE$_{25}$) copolymer for the piezoelectric. Examining the acoustic velocity of various flexible, strong, stable plastic materials that could be used as a substrate/matching layer, e.g. PET (Mylar), TPX, PEN, polyimide, we note that the velocity of polyimide is approximately 2.54 Km/sec; therefore the wavelength in polyimide, can be found from the formula $\lambda=c/f$, where c is the longitudinal acoustic velocity, f is the frequency, and $\lambda$ is the wavelength, $\lambda=2.54\times10^3/(25\times10^6)=\sim0.1\times10^{-3}=100$ microns.

Accordingly, a $\lambda/4$ (quarter-wavelength) layer of polyimide is 25 microns. As polyimide is readily commercially available in sheets of 25 micron ("1 mil") thickness, using this material provides an inexpensive film of the correct thickness to serve as the desired substrate/matching layer. Various polymers can be made in different thicknesses by spin-casting, etc., but using a commercially available film is desirable from the point of view of using a uniform and inexpensive material.

The metal electrode on the piezopolymer increases its acoustic impedance: acoustic impedance is equal to the square root of the product of the mass and elasticity of the material. Therefore, as described in "Novel Multi-Layer Polymer-Metal Structures for Use in Ultrasonic Transducer Impedance Matching and Backing Absorber Applications", M. Toda and M. Thompson, IEEE Transaction on Ultrasonics, Ferroelectrics and Frequency Control, vol. 57, no. 12, pp. 2818-2827, 2010, a thin (in relation to the wavelength) metallic layer, of density much greater than the piezopolymer and of elasticity much higher, increases the effective impedance of the metal-piezopolymer composite. The impedance of the copolymer is no longer approximately 4.5 MRayl (as previous stated), but increased due to the effect of the increased mass of the composite layer formed of the piezopolymer and electrode.

While the exact value of this new effective impedance depends on details of the relative elasticity and exact thicknesses, we can approximate the effect by calculating the increased mass per unit area of the composite layer contributed by the electrode. For the case of a gold electrode (as in the example that follows) the density of gold is 19.3 as compared to the density of P(VDF$_{75}$–TrFE$_{25}$) of 1.88. If, for example, the thickness of the piezopolymer is 10 microns and the electrode is 0.6 microns (6000 Å), we can calculate the increase in mass/area. The 10 micron layer of piezopolymer layer without the electrode had a mass M1=10*1.88. With the addition of 0.6 micron of gold, the composite mass M2=10*1.88+0.6*19.3.

As the impedance is proportional to the square root of the mass (and ignoring the increase in elasticity produced by a thin layer of gold), the "loaded" impedance of the piezopolymer layer can be approximated as the original impedance multiplied by the square root of the ratio of the after Mass M2 divided by the non-electroded mass M1 such that $Z_{loaded}=4.51*(M2/M1)^{0.5}=5.73$.

Now we calculate the impedance of a matching layer to match the loaded piezopolymer layer to tissue of impedance $Z_{tissue}=1.54$, $Z_{match}(1.54*5.73)^{0.5}=2.97$, i.e. within 1% of the impedance of polyimide ($Z_{polyimide}=3.00$).

Therefore, by adjusting the thickness and metal variety used in the electrodes and the thickness of the piezopolymer (assuming we do not need resonant operation), we can make a desired substrate material function as a matching layer. This enables making a transducer with enhanced sensitivity while simplifying the fabrication, i.e. reducing cost while improving performance.

Figure 4:
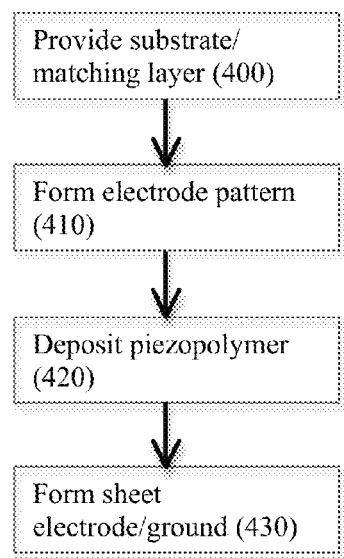
FIG. 4 shows an exemplary fabrication process according to one aspect of the present invention.

With further reference to FIG. 4, an exemplary fabrication according to one aspect of the present invention starts from providing a substrate/matching layer (400), forming electrode patterns on the substrate/matching layer (410), depositing piezopolymer onto the electroded substrate/matching layer (420), and forming another layer of electrode patterns onto the piezopolymer layer (430). The method for depositing piezopolymer lay includes spin-coating, dipping, electrospraying or other methods as may be known to one skilled in the art.

An important application of the transducer device is monitoring blood flow. In these applications, the device may be placed on or in an animal body, and be exposed to noise produced by EMI, which could come from the environment surrounding the transducer, e.g. electromagnetic radiation from other electronic devices, or from body-conducted currents arising from connections to other biomedical monitoring equipment, e.g. EKG leads. Such noise could contaminate the device's signals and reduce the accuracy of its measurements.

A well-known method of reducing EMI is "shielding", that is, placing a conducting structure between the environment carrying the EMI and the sensitive parts of a device and grounding that conductive structure so that the electric field lines or conductive paths in the device's surroundings terminate on the shield rather than on the signal-carrying electrodes (120, 121 in FIG. 2) where it could perturb the signal.

Figure 5:
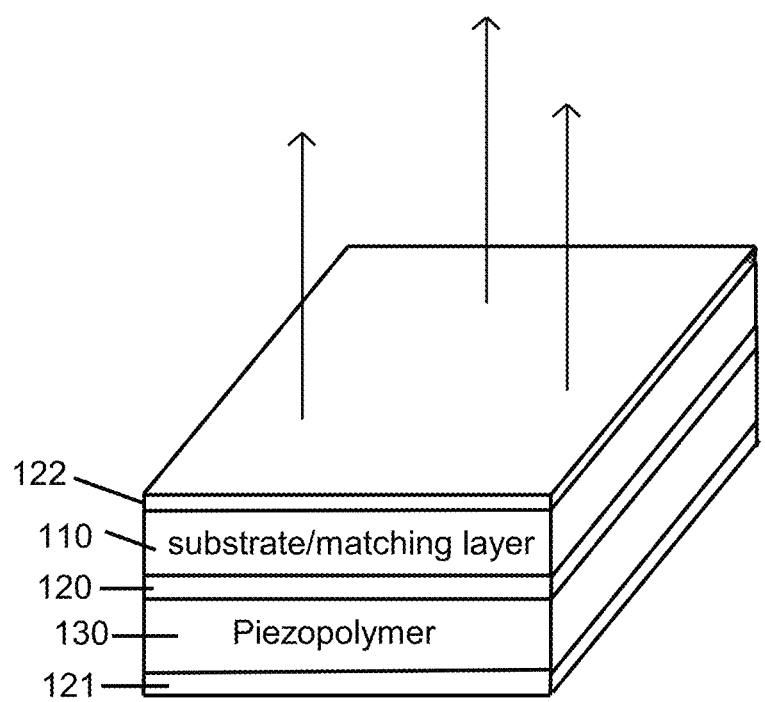
FIG. 5 shows an exemplary structure of a shielded transducer according to one aspect of the present invention.

With reference to FIG. 5, we dispose a thin metallic layer 122 on the non-piezopolymer side of the substrate/matching layer, while continuing the desired acoustic matching function of said layer. This resulting structure is identical to that shown in FIG. 2 except with the addition of the "shield" layer. This layer is conductive and thin, and is designed so that it both shields against EMI and produces acoustic matching of the substrate/matching layer. As will be described in detail in exemplary implementation, we use a conducting layer of the proper thickness and material properties so that the substrate/matching layer produces acoustic matching for optimal transducer operation while providing shielding against electromagnetic noise.

AN EXEMPLARY IMPLEMENTATION

Figure 2:
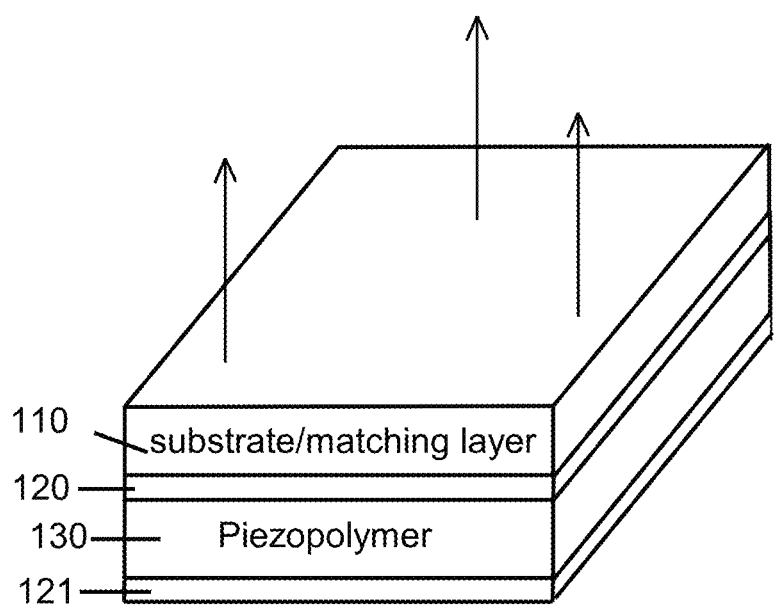
FIG. 2 shows an exemplary structure according to one aspect of the present invention. The arrows indicate the direction of the ultrasound propagation into the medium.

FIG. 2 gives an example of fabricating a transducer according to the present invention. As shown in FIG. 2, 1-mil thick polyimide is used as the substrate/matching layer (110), on which an electrode of 5000 Å gold plus a chrome adhesion layer (120) (estimated to have the effective mass of 6000 Å layer of gold) is placed in a commercially available process such as sputtering and then electroplating up to the thickness. One example of polyimide is Kapton made by Dupont. One example of the chrome adhesion layer is made by Metrigraphics. We then spin-coat a ~10-12 micron layer of piezopolymer (130) onto this substrate/matching layer (110). This structure was then annealed at 130° C. for 1.5 hours. A very thin layer of silver, ~0.05 micron in thickness (121) is then sputtered on to the piezopolymer (130) to form a ground electrode, and hysteresis-poled—bipolar triangular waves of less than 1 Hz of increasing amplitude applied to the electrodes 120 and 121. The poling waveform is gradually increased until there is no more poling current. In our exemplary embodiment, we find the maximum voltage of the poling triangular waveform that is needed to complete the poling process is about 50 Volts per micron of copolymer $P[VDF_{75}-TrFE_{25}]$.

To see the effect of the matching (substrate) layer, we use a hydrophone to measure the acoustic output from the two sides of the transducer, i.e. from the matching layer side and the piezopolymer side, as a function of frequency of 10 cycle tone bursts. We measure the acoustic pressure emitted by the transducer from its piezopolymer face (face 121 in FIG. 2 and equivalent to the usual output face used in conventional transducers (surface 121 in FIG. 1A)); the output is labeled "copoly" in FIG. 3. Then we turn the transducer around and measure the output from the "back", or substrate side of the transducer (110) in FIG. 2; the output is labeled "polyimide" in FIG. 3.

Figure 3:
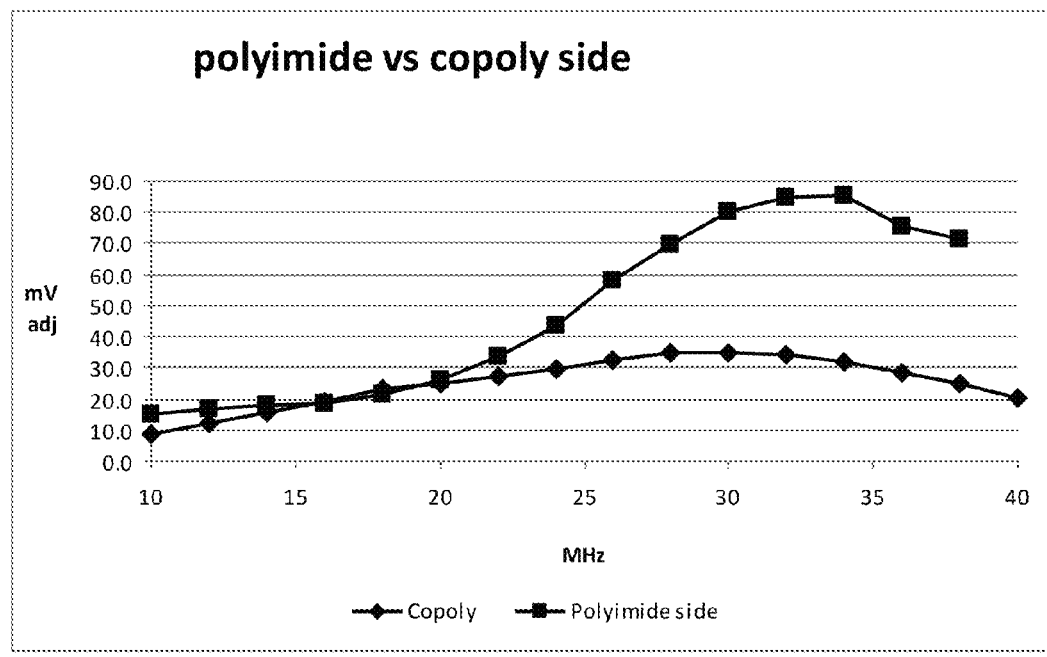
FIG. 3 shows the output as a function of frequency from an exemplary transducer fabricated according to the present invention. The vertical axis is in arbitrary units of acoustic pressure, the horizontal is frequency in MHz corresponding to the tone burst used to excite the transducer.

As shown in FIG. 3, it is clear that using the matching layer (shown in "polyimide" curve) produces more sensitivity, i.e. produces as much as 2.5 times more output per volt of excitation. The limitations of the simple theory as described early in this disclosure are also evident—rather than peaking at 25 MHz as the simple theory given would suggest, the maximum output is closer to 30 MHz. As the metal layer interfaces with and therefore affects both the piezopolymer layer and the matching layer, and therefore each layer's elasticity as well as its mass, the above observation can be explained.

This explanation of operation can be verified by changing the 1-mil Kapton to a 0.5-mil Kapton polyimide substrate, both made by Dupont. As 0.5-mil Kapton is not a matching layer, the opposite result, i.e. more output from the "copoly" side (equivalent to surface 121 in FIG. 1A and FIG. 2) than from the "polyimide" side (110 in FIG. 1A and FIG. 2), is observed.

According to one aspect of the present invention, the simple theory given above serves to "get one into the ballpark", and experimental methods are needed to optimize performance. For example, if 1-mil polyimide is desired to be used as the substrate/matching layer—because of its biocompatibility to a human body and electrical characteristics—differing thicknesses of a desired metal (such as silver, with specific gravity of 10.6 as compared to the specific gravity of polyimide of ~1.4) can be used to make transducers. The metal film thickness that is needed to achieve maximum transducer sensitivity at a desired frequency can be approximately determined by the calculation described in Para 26-28, and the final exact determination by experiment.

According to another aspect of the present invention, another way of optimizing the design for maximum output is to put down an electrode pattern in layer 120 of FIG. 2 of a metal of thickness as calculated by the above approximate method and then spin-coating differing thicknesses of piezopolymer, for example by using sequential thin spin-coats, to make transducers with a range of piezopolymer that varies around the value calculated by the approximate method. Again, after annealing and poling and the application of a ground electrode, measuring the output of each individual transducer as a function of frequency with a hydrophone will reveal the optimal thickness of piezopolymer to be used for a particular frequency and piezopolymer thickness.

According to another aspect of the present invention, we could further increase the acoustic power emitted by factor of ~1.5 by adding a relatively thick layer ~29 microns—of silver ink painted onto the "copoly" side. This acts like a reflective layer, sending more of the power through the matching layer.

In another embodiment of the present invention, if the thick layer of silver ink was painted onto the piezopolymer to serve as the electrode as well as backing, i.e. as layer 121 in FIG. 2, before the piezopolymer was annealed, the annealing process would make the silver ink particularly ruggedly adherent to the transducer—a useful characteristic.

In another embodiment of the present invention, with reference to FIG. 5, as is familiar to those skilled-in-the-art, the conductivity required of the shield layer 122 depends upon the intensity of the EMI or conducted currents. The shape of the shield layer and its thickness affects the conductivity. The formula for the resistance of a sheet of length l, width w, and thickness t is: $R=CR \times l/(w \times t)$, where R is the resistance and CR is the coefficient of Resistance. Therefore the resistance of the shield layer can be estimated by calculating the number of "squares", i.e. the ratio of l/w, multiplied by the "ohms-per-square", given by $CR/t$.

For example, using silver as the shield material, silver's coefficient of resistivity of $1.6*10^{-8}$ m (*Handbook of Chemistry and Physics*, $42^{nd}$ Edition, C. D, Hodgman, Ed., Chemical Rubber Company, Cleveland, 1960, p. 2588), a shield layer one micron of silver thick therefore will have a resistance of 0.016 ohms per square ($1.6*10^{-8}/10^{-6}$). If the shield is in the shape of a square, the resistance of the shield will be 0.016 ohms. If such a shield is used to shield against 1 mA of stray conductive current, the noise voltage produced in the shield will be (voltage equal to resistance multiplied by current) of 16 microvolts; this shield voltage, isolated from the signal electrode by the thickness of the substrate, will produce a sub-microvolt noise signal, so small as to not affect the signal which is several orders of magnitude larger.

As shown above, the ohms-per-square is inversely proportional to thickness, e.g. a 5 micron-thick shield will be characterized by 0.0032 ohms-per-square and a 0.25 micron silver shield by 0.064 ohms per square. In general, the shield thickness needed in an application will depend upon not only the material used and the shape of the shield but the magnitude of the conducted currents and/or intensity of the EMI in the particular application. In our exemplary implementation, with reference to FIG. 5, we make a 30 MHz transducer using 18 micron thick piezopolymer layer 130, and a 1-mil-thick polyimide "Upilex" characterized by an unadjusted specific density of 1.454 and an acoustic velocity of 2600 m/sec as the substrate/matching layer 110. We optimize the acoustic characteristics of the transducer 110 by fabricating a 0.3 micron silver layer electrode 120, using a 4 micron silver ground layer 121 on the piezopolymer, and making a shield layer 122 of thickness 0.7 microns. As such, these metal layers affect the acoustic characteristics of the substrate and piezopolymer so that the substrate acts as a matching layer between the piezopolymer and the medium to be insonated, as desired. Empirically, the thickness of the shield ranges from 0.25 to 10 microns.

This example transducer made by the method of fabrication here disclosed shows the simplicity of fabrication, flexible structure and improved performance. Extensions, variations as may be clear to one skilled in the art shall not depart from the scope of the present invention. For example, the depositing process of piezopolymer could also include spin-coating, dipping, electrospraying or other methods known to one skilled in the art.

Further, silver is easily electroplated to form a desired thickness and has excellent conductivity so is frequently used as shield layer. Other shield layers may be made by using copper, gold, or other such conducting materials.

Still further, the disposing of shield layer on the substrate may come before or after the disposing of piezopolymer layer.

Further, other polymer materials can be used as substrate/matching layer materials, if these materials have the required biocompatibility and availability in the desired film thicknesses, e.g. polyethylene terephthalate, or polyester.

Still further, theoretically it may be possible to have a piezopolymer that is not a piezoplastic, and though aforementioned exemplary embodiments may have suggested plasticity as a requirement in making flexible film transducers, the present invention may also be extended to non-plastic substrate/matching layers, such as gold foil that is a thin enough layer, and non-piezopolymers piezoelectrics that are thin enough, e.g. sputtered ZnO films, which may also form flexible transducers using the substrate/matching layer structure. Further, as may be known by an ordinary skill in the art, all known piezoplastics are practically piezopolymers; and all piezopolymers are practically piezoplastics. The terms piezopolymers and piezoplastics are used interchangeably, and are to be within the scope of the present invention.

Further, the disclosed art could also be extended to non-ultrasonic transducer. For example, as piezopolymers are also useful to detect temperature changes, i.e. are pyroelectrics, this disclosed method of fabrication could be useful for sensor applications in this area as well.

Still further variations, including combinations and/or alternative implementations, of the embodiments described herein can be readily obtained by one skilled in the art without burdensome and/or undue experimentation. Such variations are not to be regarded as a departure from the spirit and scope of the invention.

The invention claimed is:

1. A method of forming an ultrasonic transducer for use on a medium at an operating frequency, said method comprising:
    providing a substrate layer having a front side, a back side, and a first acoustic impedance, the back side having a uniform surface;
    disposing a first electrode layer on the back side of said substrate layer;
    depositing a piezopolymer layer on said first electrode layer with said substrate layer, said piezopolymer layer having a second acoustic impedance;
    disposing a second electrode layer on said piezopolymer layer with said first electrode layer;
    whereby said substrate layer is acoustically matching said piezopolymer material layer to the medium.

2. The method according to claim 1, wherein the piezopolymer layer comprising a copolymer material.

3. The method according to claim 2, wherein the copolymer material is a $P(VDF_x-TrFE_{100-x})$ copolymer, where x is between 65 and 82.

4. The method according to claim 1, wherein the substrate layer is biocompatible.

5. The method according to claim 1, wherein said substrate layer comprising one of the PET (Mylar), TPX, PEN, and polyimide material.

6. The method according to claim 1, wherein said method of depositing the piezopolymer layer including one of spin-coating, dipping, and electrospraying.

7. The method according to claim 1, further comprising disposing an additional layer of silver ink onto said second electrode layer to act as a reflective layer.

8. The method according to claim 7, wherein said method of disposing said additional layer is painting.

9. The method according to claim 1, further comprising adjusting the thickness of said second electrode layer based on the thickness of said substrate layer, said operating frequency and the impedance of said medium.

10. The method according to claim 1, further comprising adjusting the thickness of said piezopolymer layer based on the thickness of said first electrode layer, said operating frequency and the impedance of said medium.

11. A method of forming an ultrasonic transducer for use on a medium at an operating frequency, said method comprising:
    providing a substrate layer having a front side, a back side, and a first acoustic impedance, the back side having a uniform surface;
    disposing a first electrode layer on the back side of said substrate layer;
    depositing a piezopolymer layer on said first electrode layer with said substrate layer, said piezopolymer layer having a second acoustic impedance;
    disposing a second electrode layer on said piezopolymer layer with said first electrode layer; and
    disposing a shield layer on the front side of said substrate layer;
    whereby said substrate layer is acoustically matching said piezopolymer material layer to the medium.

12. The method according to claim 11, wherein the piezopolymer layer comprising a copolymer material.

13. The method according to claim 11, wherein the shield layer is made from silver.

14. The method according to claim 11, wherein the disposing of shield layer is electroplating.

15. The method according to claim 11, further comprising adjusting the thickness of said shield layer based on the thickness of said substrate layer, the thickness of said piezopolymer layer, the thickness of said first and second electrode layer, said operating frequency and the impedance of said medium.

* * * * *